United States Patent [19]
Rutter et al.

[11] Patent Number: 5,486,462
[45] Date of Patent: Jan. 23, 1996

[54] DIFFERENTIATIVE EXPRESSION MODULES

[75] Inventors: William J. Rutter; Michael D. Wlaker, both of San Francisco, Calif.; Thomas Edlund, Umeå, Sweden; Anne M. Boulet, San Francisco, Calif.

[73] Assignee: The Regents of the University of California, Oakland, Calif.

[21] Appl. No.: 900,512

[22] Filed: Jun. 17, 1992

Related U.S. Application Data

[63] Continuation of Ser. No. 768,345, Sep. 30, 1991, abandoned, which is a continuation of Ser. No. 327,366, Mar. 22, 1989, abandoned, which is a continuation of Ser. No. 196,781, May 18, 1988, abandoned, which is a continuation of Ser. No. 674,225, Nov. 23, 1984, abandoned.

[51] Int. Cl.$^6$ .............................. C12N 5/06; C12N 15/11; C12N 15/17; C12N 15/67
[52] U.S. Cl. .................. 435/69.1; 435/172.3; 435/240.1; 435/320.1; 536/24.1; 935/13; 935/34; 935/36
[58] Field of Search .................. 435/69.1, 6, 320.1, 435/172.3, 69.4, 240.1; 536/27, 24.1; 935/22, 23, 32, 34, 36, 76

[56] References Cited

U.S. PATENT DOCUMENTS 4,663,281  5/1987  Gillies et al. ......................... 435/69.1

OTHER PUBLICATIONS

Laimins, L. et al. Nov. 1982 PNAS 79:6453.
Walker, M. et al. Dec. 1983. Nature 306:557.
Palmiter et al. (1983) Science 222:809–14.
Chen, I. et al. Nature 309:276 (May 1984).
de Villiers, J. et al 1982. NAR 10:7965.
Barnerji, J. et al, *Cell* 33:729–740, (Jul., 1983), "A Lymphocyte Specific Cellular Enhancer is Located Downstream of the Joining Region in Immunoglobulin Heavy Chain Genes".
Gillies, S. et al, *Cell* 33:717–728, (Jul., 1983), "A tissue–specific Transcription Enhancer Element is Located in the Major Intron of a Rearranged Immunoglobulin Heavy Chain Gene".
Queen, C. et al, *Cell* 33:741–748, (Jul., 1983), "Immunoglobulin Gene Transcription is Avtivated by Downstream Sequence Elements".
*Science* 224:588–589, (May, 1984), "New Clues to Gene Regulation".
Oi, V. et al, *Proc. Natl. Acad. Sci.* 80:825–829, (Feb. 1983), "Immunoglobulin gene expression in transformed lymphoid cells".
Stafford, J. et al, *Nature* 306:77–79 (Nov. 1983), "Cell–type specific expression of a transfected immunoglobulin gene".
Berg, P. et al, *Molec. & Cellul. Biol.* 3:1246–1254, (Jul., 1983), "Differential Activation of the Mouse B–Globin Promoter by Enhancers".
Kondoh, H. et al, *Nature* 301:440–442, (Feb. 1983), "Tissue–specific Expression of a cloned chick S–crystallin gene is mouse cells".
de Villers, J. et al, *Nuc. Acids. Res.* 9:6251–6264, (1981), "A small segment of polyoma virus DNA enhances the expression–of a cloned B–globin gene over a distance of 1400 base pairs".
Tyndall, C. et al, *Nucl. Acids Res.* 9:6231–6249, (1981), "A region of the polyoma virus denome between the replication origin and late protein–coding sequences is required in dis for both early gene expression and viral DNA replication".
Neuberger, M., *EMBO* 2:1373–1378, (1983), "Expression and regulation of immunoglobulin heavy chain gene transfected into lymphoid cells".
Karin, M. et al, *Cell* 36:371–379, (Feb. 1984), "Activation of a Heterologous Promoter in Response to Dexamethasone and Cadmium by Metallothionein Gene 5'–Flaning DNA".
Scholer, H. et al, *IMBO* 4:3005–3013, (1985), "Cell type–specific transcriptional enchancement in vitro requires the presence of trans–acting factors".
Laimins, L., *Proc. Natl. Acad. Sci.* 79:6453–6457, (1982), "Host–specific activation of transcription by tandem repeats from simian virus 40 and Moloney murine sarcoma virus".
McKnight, S. et al, *Science* 217:316–324, (Jul., 1982), "Transcriptional Control Signals of a Eukaryotic Protein–Coding Gene".
Edlund, T., *Science* 340:912–916, (Nov. 1985), "Cell–Specific Expression of the Rat Insulin Gene: Evidence for Role of Two Distinct 5' Flanking Elements".
Ott, M. et al, *EMBO* 3:2505–2510, (Nov. 1984), "Tissue–specific expression is conferred by a sequence from the 5' end of the rat albumin gene".
Walker, M. et al, *Nature* 306:557–561, (Dec. 1983), "Cell–specific expression controlled by the 5'–flanking region of insulin and chymotrypsin genes".

*Primary Examiner*—Robert A. Wax
*Assistant Examiner*—Dian C. Jacobson
*Attorney, Agent, or Firm*—Phillips, Moore, Lempio & Finley

[57] ABSTRACT

More effectively controlled expression of DNA sequences in coding desired heterologous proteins is achieved in differentiated eucaryotic cells by methods of this invention. Disclosed herein are control modules derived from selectively expressed genes of eucaryotic cells, such as, for example, insulin and chymotrypsin genes. These control elements contain cis-acting sequences which are responsive to indigenous trans-acting substances in the differentiated cell, which substances control the expression of the gene. Such cis-acting elements occur within the promoter region of such selectively expressed genes, and also in the five prime flanking region of the coding sequence in a position upstream of the promoter. These upstream enhancer sequences may be located using the methods disclosed herein, and ligated into differentiative expression modules for production of desired heterologous proteins.

12 Claims, 5 Drawing Sheets

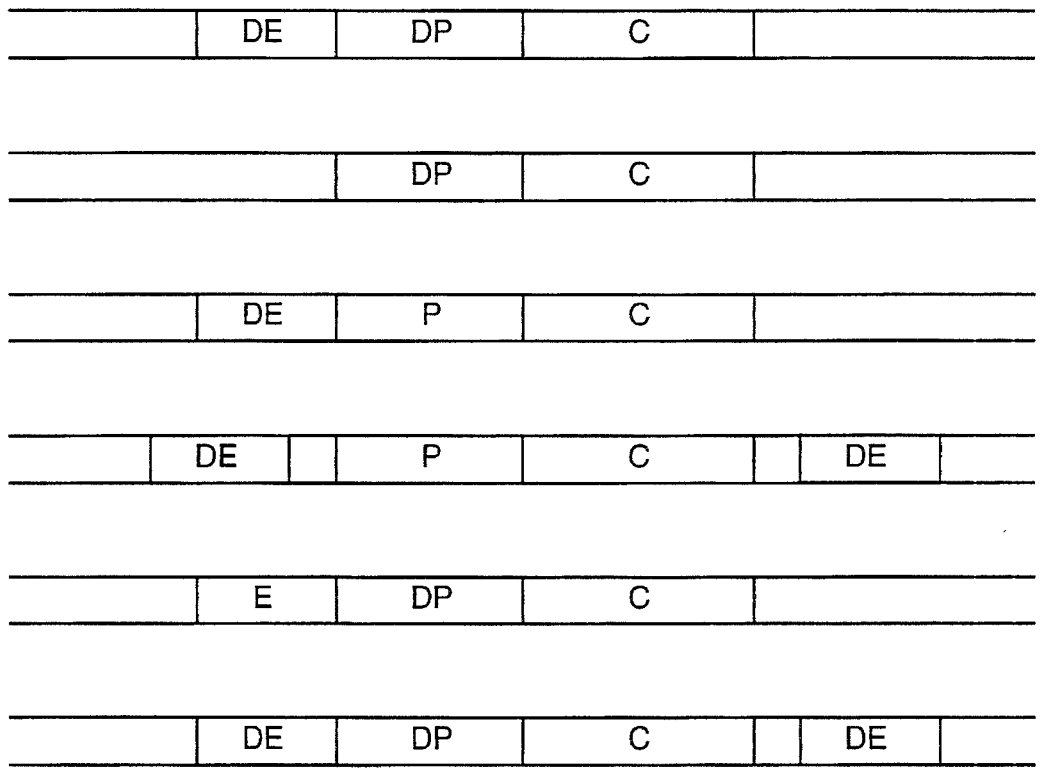
FIG._1

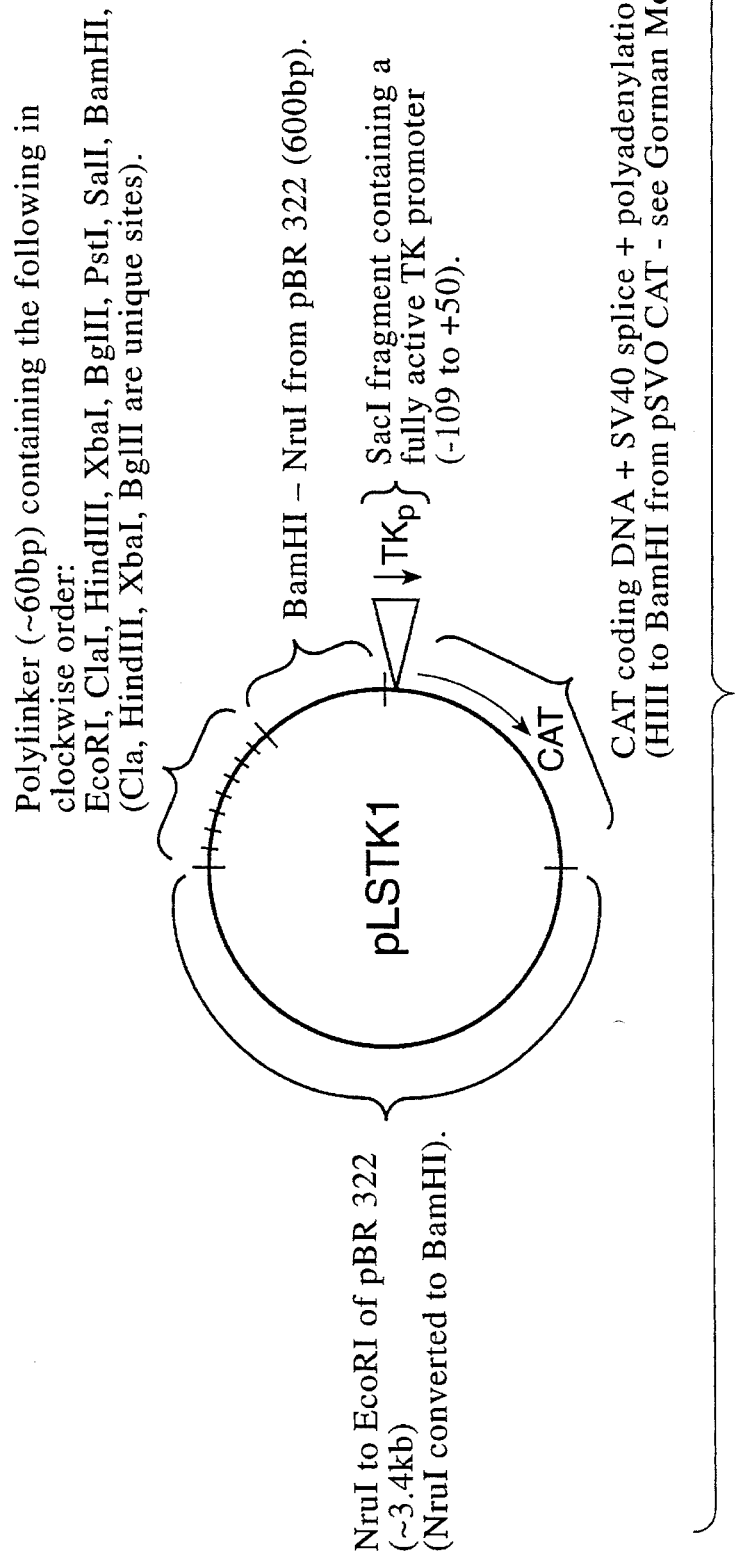
FIG._2

```
              -165                        -140                   -120
GUINEA PIG    CTGCAGACCCCAGCACCAGGGAAATGATCCAGAAATTGCAACCTCAGCCCCC-TGGCCATCTGC
RAT I         CTGCAGACTTAGCACTAGCCAGGGAAATGATCCAGAAATTACAGCTTCAGCCCCTCTGCCATCTGC
RAT II        CTGCAGACCTAGCACCAGGCAAGTG-TTTGGAAATTACAGCTTCAGCCTTCTCGCCATCTGC
HUMAN         CCACAGACCCAGCACCAGGGAAATGGTCCGGAAATTGCAGCCTCAGCCCCC--AGCCATCTGC
DOG           CCGCAGACCCAGCACTGGGGAAATGATCCAGAAATTGCAGCCTCAGCCTCC--GGCCATCTGC

-100                     -80                  -60
              TGATGCCACCACCCCCCAGGTCCCT-AATGGGCCTGGTGGCAGAGGTT------GGGAAGA
              CTAC-CTACCCTCCTAGAGCCCTTAATGGGCCAAAACGGCAAAGTCCAGGGGCAGAGAGGA
              TGAT-CCA------CCCTTAATGGGACAAACAGCAAAGTCCAGGGTCAGGGGGG
              CGACCCCCCCCACCCC-AGG-CCCT-AATGGGCCGGCCAGGGGTTGACAGGTAGGGAGA
              CACCCCC-------------------TCAT-GGCCAGGCCG-------------

-40                   -20                  -1
              TGGGCTCAG-GGCTATATAAAGTCCACAAGGACCTAAG-AGCCCCC
              GGTGCTTTG-GAC--TATAAAG-CTAGTGGAGAGACCCAGTAACTCCC
              GGTGCTTTG-GAC--TATAAAG-CTAGTGGGATTCAGTAACCCCC
              TGGGCTCTGAGAAC--TATAAAG-CCAGTGGGGGCCCAGCAGCCCTC
              TGGGCTCGGGGAGC--TATAAAG--CAG-GAGGGTCCAGCAGCCCCC
```

FIG._3

```
                                                                                                                        300
RAT I     CAGGGACAAAGATACCAGGTCCCC-AACAAACTGCAAC-TTTCTGGGAAAATGAGGTGGAAAA-TGCTCAGCCAAG
RAT II    AAGGGACAAAGTTACTAGTCCCCAACAACTGCAGC-CTCCTGGGAATGATGTGGAAAAATGCTCAGCCAAG
HUMAN     CAGCG-CAAAGAGCCCCGCCCTGC-AGCCTC--CAGCTCTCCTGG---TCTAATGTGGAAAGTGGCCCAGGTGAG

250
RAT I     GAAAAGAGGGCCCTTACCCTCTCTGGGACAA-TGATTG-TGCTGTGAACTGCTTCA---TCAGGCCATCTG--- 
RAT II    GACAAAGAAGGCCTCACCCTCTCCCCTGAGACAA-TGTCCCCTGCTGTGAACTGGTTCA--TCAGGCCACCCAGGA
HUMAN     G----GCTTTGCTCTC-CTGAGACATTTGCCCCCAGCTGTGAGCTGTGAGCAGTCTGGCCACCGG--

200
RAT I     GCCCCTTGTTAATAATCTAATTACCCTA-GGTC-TAAGT-AGAGTTGTTGACGTCCAATGAGCGCTTTCTGCAG
RAT II    GCCCCT-ATTAAGACTCTAATTACCCTA-AGGC-TAAGT-AGAGGTGTTGTCCAATGAGCACTTTCTGCAG
HUMAN     GCCCCTGGTTAAGACTCTAATGACCCGCTGGTCCTGAGGAAGAGAGGTGCTGACGACCAAGGAGATCTTCCCACAG

100
RAT I     ACTTAGCACTAGGCAAGTG-TTTGAAATTACAGCTTCAGCCCCTCTCGCCATCTGCCTACCCCTCCTAG
RAT II    ACCTAGCACCAGGCAAGTG-TTTGGAAAACTCAGCCAGCCCCCTCTCGCCATCTGCCATCTGATCCATCC-
HUMAN     ACCCAGCACCAGGGAAATGGTCCGGAAATTGCAGCCTCAGCCCCCA--GCCATCTGCCGACCCCCACCCC--

RAT I     AGCCCCTTAATGGGCCAAACGGCAAAGTCCAAGGCAGAGAGGAGGTGCTTTG-GACTATAAAG CTAGTGGAGA
RAT II    ----TTAATGGGACAAACAGCAAAGTCCAGGGGTCAGGGGGTGCTTTG-GACTATAAAG CTAGTGGGGA
HUMAN     -GCCC-TAATGGGCCAGGGGTTGACAGGTAGGGAGATGGGCTCTGAGACTATAAAG CCAGCGGGGGA
                              CAP                                 ATA BOX

RAT I     CCCAGTAACTCCC
RAT II    TTCAGTAACCCCC
HUMAN     CCCAGCAGCCCTC
```

FIG._4

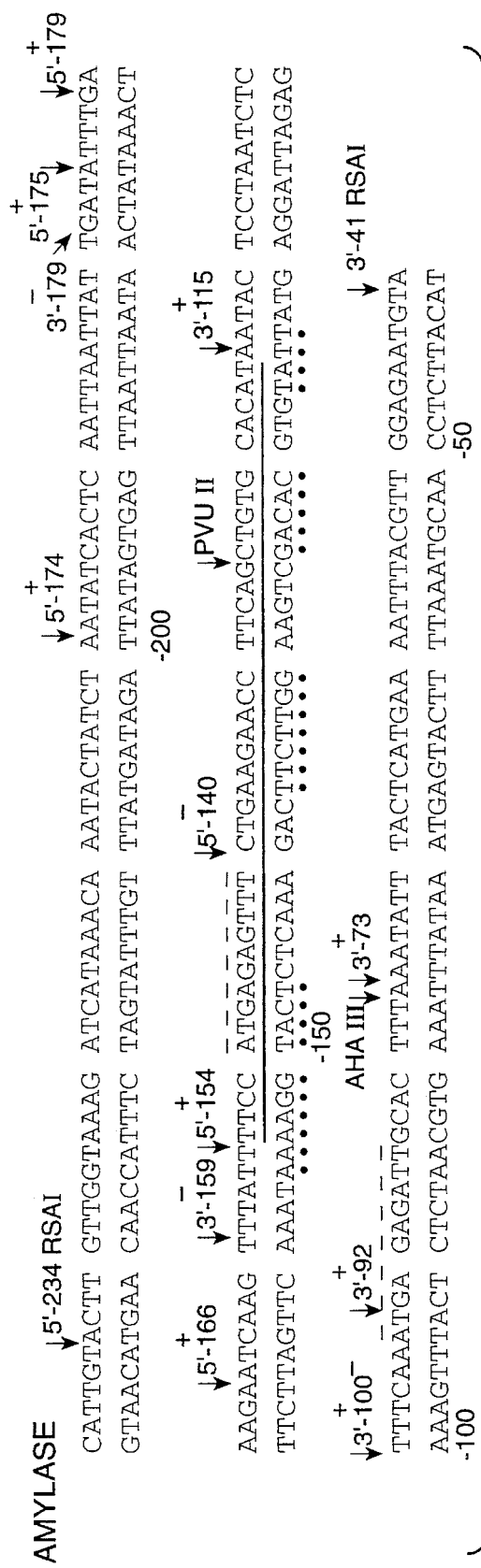
FIG._5A
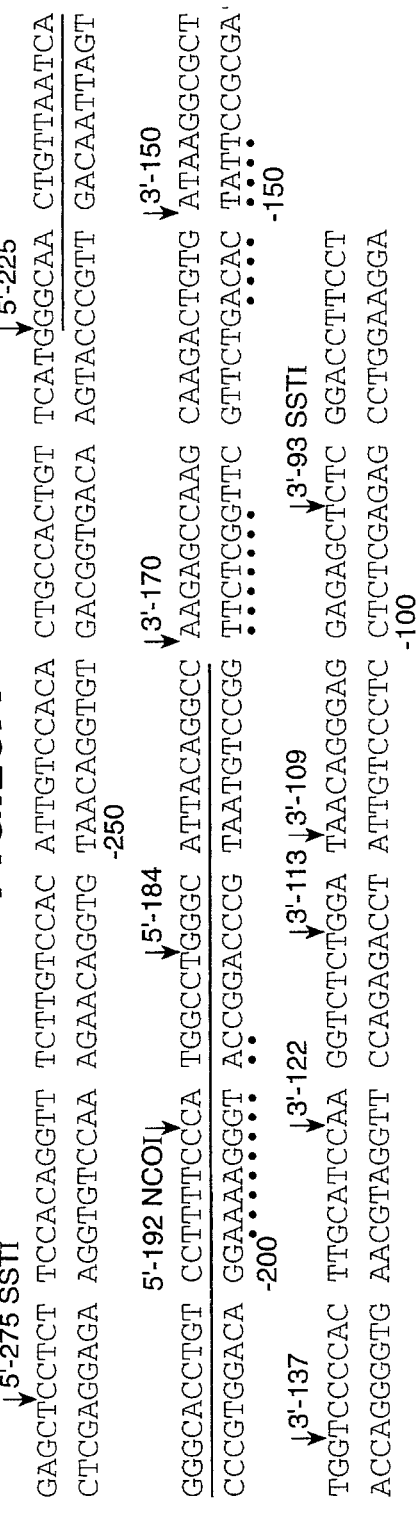
FIG._5B

DIFFERENTIATIVE EXPRESSION MODULES

This application is a continuation, of application Ser. No. 07/768,345, filed Sep. 30, 1991, now abandoned, which is a continuation of application Ser. No. 07/327,366 filed Mar. 22, 1989, now abandoned, which is a continuation of application Ser. No. 07/196,781 filed May 18, 1988, now abandoned, which is a continuation of application Ser. No. 06/674,225 filed Nov. 23, 1984, now abandoned.

TECHNICAL FIELD

The invention herein relates to the field of protein production and host modification using recombinant DNA technology. In particular, the invention provides cis-acting DNA sequences juxtaposed to any desired coding sequence. These cis-acting DNA sequences provide a means for selectively regulating expression of the linked coding sequence in differentiated eucaryotic cells.

BACKGROUND ART

Standard techniques of biotechnology permit the expression of desired sequences in suitable host cells by providing control sequences operable in these hosts. Specifically, if the production of a particular protein is desired in a bacterial host, the coding sequences for that protein are linked to bacterial promoter and ribosome binding site encoding sequences. Similarly, expression in eucaryotic hosts can be obtained by linking the coding sequence to, for example, yeast derived control sequences for expression in yeast, or to promoters derived from viruses normally infecting mammalian hosts to effect mammalian host cell expression.

While it has been possible to culture bacterial hosts transformed with vectors which effect expression to produce high levels of foreign proteins—sometimes corresponding to as much as 50% or more of total cell protein, eucaryotic recombinant hosts, in general, are not so productive. The presently available control systems are derived from viral sources, and ligated upstream from desired coding sequences for use in these cells. The eucaryotic differentiated transformants provide production levels which are several orders of magnitude lower than those obtained for the specialized products of these cells in vivo. This result is true despite the fact that differentiated cells may produce extremely large amounts of specialized products, endogenously. Erythrocytes for example, produce and secrete hemoglobin in amounts approaching 90% of total cell protein; pancreatic cells secrete amylase in total amounts approximating their cell mass. Protein production by recombinant eucaryotes is substantially lower in amount.

It is often desirable, nevertheless, to use eucaryotic, including mammalian, hosts for protein production since the processing effected by these cells, including e.g., glycosylation and/or proper folding of the protein products, may be a needed accompaniment to production of the peptide sequence. TPA and Factor VIII are examples of such glycosylated proteins. Thus, a method to increase the level of production of a desired gene product in cell cultures of eucaryotic cells would be of immense practical benefit.

Techniques using recombinant DNA also offer the possibility of host cell modification, i.e., it is often feasible to confer on the host cell some desirable property either with respect to the survival of the organism or, in the case of isolated cell cultures, with respect to maximizing an enzyme activity needed for the production of a secondary product. For example, increases in the level of enzymes responsible for the production of alcohol in yeast would improve the properties of the host organism as an industrial tool. In an example perhaps more relevant to the cell-specific sequences of the invention, bone marrow cells used for transplant might be encouraged to produce large amounts of immunosuppressant directed against T cells. In this context, also, regulation or enhancement of particular coding sequence expression would be advantageous.

Two major approaches have been taken to increase the level of production of a desired protein in eucaryotic hosts. In one, the desired coding sequence is ligated to a sequence which is capable of being amplified under certain selective conditions. The best known example of such an approach employs the sequences encoding dihydrofolate reductase (DHFR) which are amplified in the presence of the inhibiting drug methotrexate. In the second approach, expression constructs are provided with a viral-derived control element located 100–300 bp upstream from the transcription start site in the virus, which has been designated an "enhancer". The enhancers are short, cis-acting sequences which cannot themselves initiate transcription, but can potentiate transcription from a variety of promoters. Their effectiveness is relatively independent of position in the vector and of orientation. Such enhancers apparently operate in a manner which is not predictably dependent on the nature of the host cell. For example, the polyoma enhancer is functional in any differentiated mouse cell but not in undifferentiated embryonic cells.

It is recognized that sequences associated with a native gene may show some preference for transformant hosts which represent cells to which the gene is endogenous. For example, myeloma cell transformants, produce higher levels of immunoglobulin K chain than do correspondingly transformed fibroblasts (Oi, V., et al, *Proc Natl Acad Sci* (USA) (1983) 80:825), and lens cells microinjected with the chick delta crystalline gene produce more of this protein than do similarly injected fibroblasts (Kondoh, H., et al, *Nature* (1983) 301:440).

Some progress has been made in identifying the DNA sequences associated with this specificity. It has recently been shown that an intron sequence in the coding region for immunoglobulin heavy chain contains a lymphocyte specific enhancer which apparently results in higher levels of heavy chain production in B-lymphocyte derived (myeloma) cells than in other transformants such as HeLa cells. The enhancing effect of this intron sequence was also studied with respect to production of SV40 T-antigen under control of the SV40 promoter (Banerji, et al, *Cell* (1983) 33:279) and shown to be effective in regulating expression of the T-antigen gene in lymphocyte derived myeloma cells, but not in HeLa cells. It has also been shown that DNA sequences from the J-C region of the immunoglobulin gene are cis-acting independently of orientation and are active in mouse B cells but not in mouse fibroblasts (Gillies, S. D., et al, *Cell* (1983) 33:717). See also Queen, C, et al, *Cell* (1983) 33:741.

If cell-specific DNA sequences could be employed so as to increase expression of foreign coding sequences to a level comparable to that attained for sequences natively associated with specialized cells, a quantum improvement in production of foreign proteins could be achieved. However, none of the foregoing DNA sequences provide a portable enhancer fragment which can be relied upon to increase the level of protein production in a particular cell type transformant host to such levels. Thus, while the possibility exists that genes native to differentiated eucaryotic cells may contain control sequences which are cell-specific, and which are supplementary to the usually considered requirements for expression such as promoter, polyadenylation signal, etc., no reliable source for such cell-specific enhancing sequences has been found. The present invention provides such sequences which can be used to effect enhanced expression in specific desired transformant host cell types.

DISCLOSURE OF THE INVENTION

The invention provides an improved control module designed to control and elevate the level of expression in a differentiated eucaryotic cell. When properly disposed with respect to a coding sequence for a desired protein, eucaryotic cells which normally and selectively express the gene from which the control module is derived can be stimulated to high levels of production of this protein. It is believed that this is due to the specific interaction between the differentiative control module and factors indigenous to these corresponding cells. The increased levels of the desired protein may be significant in order simply to obtain large amounts of it per se, or to confer a desirable characteristic on the transformed host.

The differentiative control modules of the invention comprise either at least one differentiative enhancer module or a differentiative promoter module or both. The enhancer module is a DNA sequence which is capable of increasing the production levels of protein encoded by a DNA sequence which is on the same polynucleotide molecule. The relative positions of the two sequences is comparatively uncritical. The differentiative promoter module is a DNA sequence which mediates the initiation of transcription—i.e., is a promoter in the usual sense, but which is derived from a gene which is selectively expressed in a differentiated cell (e.g., the insulin gene in pancreatic β-endocrine cells) and which contains internal sequences responsive to factors responsible for selective high level production of the protein natively encoded downstream from the promoter (i.e., insulin in this case). As it appears that enhancer sequences commonly reside immediately upstream of the promoter in such differentiative genes, the simplest form of the differentiative expression system of the invention would be obtained by ligating an extended 5' flanking region derived from the selectively expressed gene to the coding sequence for the desired protein.

Thus, in one aspect, the invention relates to a method for regulating heterologous protein production in a eucaryotic differentiated host cell, which method comprises providing a DNA sequence in which the coding sequence for the desired protein is in operable linkage to a differentiative control module. The regulation of production levels is then obtained by culturing cells transformed with this expression system. The transformed cells must be eucaryotic differentiated cells which correspond to the type from which the differentiative control module was derived or which are modified to produce the putative trans-acting factor(s) that interact with the cis-acting differentiative control sequences.

In other aspects, the invention relates to the differentiative expression system sequence which contains the control module, to expression vectors containing it, to cells transformed with these sequences or vectors, and to the heterologous protein products of these transformed cells.

The invention also relates to a method for locating the differentiative enhancer sequences, and to an improved method for assay of these sequences.

BRIEF DESCRIPTION OF THE DRAWINGS

FIG. 1 shows, diagramatically, the permutations of differentiative expression systems of the invention.

FIG. 2 shows a schematic diagram of pLSTK1.

FIG. 3 shows the DNA sequences of the proximal 5' flanking region of the selectively expressed insulin gene from several species.

FIG. 4 shows extended 5' flanking regions for ratI, ratII and human insulin genes.

FIG. 5 shows extended 5' flanking regions for the amylase and chymotrypsin genes.

MODES FOR CARRYING OUT THE INVENTION

A. Definitions

As used herein, "differentiative expression system" refers to a DNA sequence which contains the coding sequence for a desired protein operably linked to a "differentiative control module". The system is particularly designed to effect expression of the protein encoding sequence in a eucaryotic differentiated cell which corresponds to the particular eucaryotic differentiated cell that is characterized by the expression of the gene from which the differentiative control module is derived.

The "differentiative control module" is defined by its components. It may contain either a "differentiative promoter module", one or more "differentiative enhancer modules" or both.

As used herein, and, in particular, in the following definitions, "derived from" means having substantially the same nucleotide sequence as, in the sense that the derived sequence can accept and respond to trans-acting factors within the cell in a manner similar to the sequences in the gene from which it is derived.

"Differentiative promoter module" refers to a promoter which is derived from a gene which is selectively expressed in a eucaryotic differentiated cell, and which contains elements which permit it to respond selectively to factors which are indigenous to that cell. "Selectively expressed" refers to a gene which encodes a protein which is produced in some, but not all eucaryotic differentiated cells. Unlike the enhancer module, the promoter may or may not be operable in host cells which do not correspond to those characterized by expression of its gene of origin. Thus, a promoter derived from the insulin gene of pancreatic endocrine cells may or may not be able to effect the expression of a properly ligated coding sequence in other mammalian hosts. However, as shown below, the promoter contains sequences which are responsive to trans-acting control substances contained in the endocrine cells. As a part of the "differentiative control module" it is the sequence which serves the promoter function in effecting expression of the desired protein.

"Differentiative enhancer module" refers to a DNA sequence derived from a similar gene to that described above, which is capable of responding to cell-specialized trans-acting substances and enhances expression of the relevant coding sequence, but cannot, by itself effect expression. The enhancer amplifies the effects of the classical required controls, notably the promoter.

Both the differentiative promoter module and differentiative enhancer module may be derived from the 5' flanking region of a selectively expressed gene. The "5' flanking region" of such a gene refers to the DNA sequence immediately upstream of the transcribed sequence. (DNA sequences are generally written in a 5'–3' direction.) Sequences derived from the 5' flanking sequence can provide both the differentiative enhancer sequences and the differentiative promoter module. The 5' flanking sequence includes promoter sequences upstream of the transcription initiation site, which is roughly a region within 100 bp 5' of the initiation site. The promoter sequence includes the TATA box which is about 30 bp upstream and the concensus sequence CCAAT about 70–80 bp upstream, as well as a required region 80–110 bp upstream from the initiation site. The presence of differentiative sequences in, or upstream of, this promoter region has not been noted previously in differentiated eucaryotic cells.

"Derived from", in this context, does not refer to a physical derivation, but rather sequences which are the same as, or substantially (functionally) similar to, those found in the native gene. Specifically the module sequences which are "derived from" a region in a selectively expressed gene may be synthesized chemically, enzymatically, or in any other manner known in the art, as well as prepared by cloning the relevant sequences.

"Operable linkage" or "operably linked" refer to situations wherein the factors in question are juxtaposed in such a way to enable them to perform their expected function. Thus, a promoter "operably linked" to a coding sequence refers to a situation wherein the promoter is capable of effecting the transcription of the sequence. A differentiative enhancer module "in operable linkage" to an expression system refers to situations wherein the enhancer module is capable of performing this function with regard to the expression system. Requirements for operable linkage may be very strict or relatively flexible. The promoter sequences, for example, whether differentiative or not, appear to be effective only if located proximally 5' of the coding sequence, and only in the correct one of the two possible orientations. The enhancer module sequences are cis-acting and therefore must be present on the same molecule of DNA as the expression system, but appear to be operable when placed either upstream or downstream within a variable distance from the coding sequence, and are functional in either possible orientation. There appears to be, however, an optimum location for such enhancer sequences. The differentiative control module must be placed so that its components are in operable linkage to the coding sequence.

"Expression system" refers to a DNA sequence which contains both the coding sequence and appropriate control sequences which are capable of transcribing and translating the coding DNA and thus of effecting the production of a desired protein. Normally, of course, the coding sequences can derive from a gene of any species origin; the control sequences on the other hand need to be compatible with the host. In any event, the expression system provides all the elements necessary for the production of a desired protein at some level in the host. For eucaryotic cells, a promoter, and often a terminator are required. It should be noted that the expression system may include any working promoter such as, for example, a viral promoter, or a differentiative promoter, derived from the cell-specialized or "selectively expressed" gene characterizing the corresponding cells which will be used as hosts. In the latter case, a portion of the expression system is also a part of the differentiative control module.

The terms "host cells", "transformant host cells", "transformed hosts", and "host" are used interchangeably and refer to cells whose DNA content has been or is intended to be augmented by additional DNA sequences introduced by transformation or other means of effecting controlled DNA entry into cells. The most common technique is transformation with DNA or a DNA complex, mediated, for example, by calcium phosphate precipitation. However, other means of effecting this result are available, such as conjugation in yeast cells, or viral infection.

"Recombinant transformed hosts" means specifically those hosts which have been transformed with DNA sequences which have been constructed using the in vitro techniques of recombinant DNA technology.

Also in connection with the foregoing, "host cells" refers not only to the cell originally accepting the DNA sequence, but also the progeny thereof. Indeed, "cells", "cell cultures" and "cell lines" are used interchangeably and indicate this entire population as well as single members thereof. It is understood that the progeny of a particular transformed host may not be precisely identical in DNA content to the parent cell, as modifications occur either accidentally, or by deliberate mutation. However, all of these modified progeny are included when still harboring the DNA sequence with which they were transformed, and when operating on that sequence in a manner analogous to that characterizing the parent cell. Specific modified progeny which are included are those wherein transforming vectors have been incorporated into the chromosomal DNA of the host.

The transformed hosts of the invention are eucaryotic differentiated cells, The hosts must "correspond" to the nature of the differentiative control module of the transforming DNA, That is, the differentiative control sequences must be derived from the selectively expressed gene whose expression characterizes the host cell. "Corresponding" cells may be those natively associated with the differentiative module, or cells which have been modified to produce the relevant trans-acting factors.

B. General Description

B.1. Components of the Control Module and Utility

The invention takes advantage of the cis-acting elements which are responsible for the genetic expression which characterizes eucaryotic differentiated cells. In general, a differentiated cell is characterized by a stable state where only a portion of the genetic repertoire is expressed, and where the expression of a particular gene results in the production of significant levels of a particular protein. Production levels vary according to the type of cell, some producing extraordinarily high levels of this protein, others controlling production in response to requirement. Examples of such differentiated cells in mammals include endocrine cells which secrete protein hormones into the blood stream, such as those cells secreting insulin, glucagon, somatostatin, growth hormone, luteinizing hormone, follicle stimulating hormone, and the like, or B-lymphocytes which secrete immunoglobulins. Some differentiated cells secrete proteins to locations external to the homeostatic environment of the organism, such as the pancreatic exocrine cells which secrete chymotrypsin, pepsin, amylase, and trypsin into the digestive system. Other differentiated cells express genes or proteins which are not secreted, such as red blood cells which produce globin, and lens cells, which produce crystallin.

These differentiated cells have not been commonly used as recombinant hosts largely because techniques for efficient transformation and cell growth have not been perfected. However, they offer some distinct advantages as producers of desired proteins because their inherent characteristics are such that a particular protein is expressed at high level when the cell has been differentiated, and, indeed, the differentiated nature of the cell is characterized by the selective production of the protein. In addition, these cells may secrete or internalize the protein produced. The present invention seeks to take advantage of the systems which result in this selective genetic expression and localization of the resulting protein (intra- or extracellular) to effect the production of a desired protein.

The utility of the techniques and materials of the invention is thus clear. They can be used to effect the synthesis of such useful proteins as, for example, the interferons, such as leukocyte, fibroblast, or γ-interferons, growth factors such as epidermal growth factor or nerve growth factor, blood factors such as urokinase or tissue plasminigen activator, peptide sequences which can be used as vaccines such as those associated with viral coat proteins, lymphokines, such as lymphotoxin, tumor necrosis factor, or interleukin, regulatory proteins, such as follicle stimulating hormone, and useful enzymes such as oxidases, dehydrogenases, and isomerases. The array of suitable desired useful proteins is extensive.

While cell lines are available which produce selectively produced proteins, including many proteins which are among those listed as desired peptides above, the invention offers several advantages over "native" production of these proteins by culturing the appropriate differentiated cell. First, it permits particularly effective differentiative control modules to be used with respect to any desired coding sequence, not just that for the cognate protein. An advantage of the differentiative control sequences of the invention in the corresponding cell types over those used in the more versatile host systems currently used in recombinant work is that the use of viral promoters and enhancers is eliminated, thereby obviating the dangers that are associated with employing DNA sequences of viral origin. Second, the methods of the invention permit the development of techniques for culture and growth of one particularly successful differentiated cell line to be put to use in connection with the production of the entire range of desired peptides, rather than limitation to the cognate protein produced by the host. Finally, cultured differentiated cells often produce their native cognate proteins at levels much lower than those ordinarily produced by these cells.

In the method of the invention, the coding sequence for the desired protein is ligated to a differentiative control module so as to be in operable linkage with the elements of the control module. The differentiative control module may or may not contain the promoter that controls the transcription of the desired heterologous sequence. Indeed, if desired, a viral promoter is consistent with use of the enhancer portion of the differentiative control module of the invention. Conversely, the differentiative control module may contain only a differentiative promoter, and may contain no enhancers at all, or only viral or non-specialized enhancers. In a third alternative, both the operating promoter and the enhancers are differentiative and together comprise the differentiative control module (see FIG. 1).

Indeed, perhaps the simplest construction of the differentiative control module of the invention employs the 5' flanking sequence of a selectively expressed gene, of such length as to include not only the promoter region, but also the enhancer elements upstream of the promoter. This fragment, which will include from about −1 to about −300 (−1 being the first nucleotide upstream of the transcription initiation site) of the selectively expressed gene appropriate to the intended host can be excised using restriction enzymes, cut back with exonucleases, if necessary, and placed directly upstream of a desired coding sequence. Alternatively, only the promoter region might be used, or, a promoter of viral origin may be ligated immediately upstream of the coding region, and the enhancer elements separately excised and placed in operable linkage to the expression system, whether that system includes a differentiative promoter or not.

In order to effect operable linkage, the positioning of the enhancer elements is less critical than the positioning of the promoter. It is well understood in the art that the essential elements of the promoter must lie immediately upstream of the transcribed sequence, and are operable in only one of the two possible orientations. While the enhancer elements may very well work best in their native orientation, e.g., immediately 5' of the promoter, these sequences can be excised and ligated at various distances from the expression system and in either possible orientation, and still exhibit enhancer activity. The enhancer activity shown at one position or another may be greater or less. However, it appears that positioning within about 2 kb of the expression system results in at least some level of enhancement. It may also be possible to ligate these sequences into the intra-expression system region itself, e.g., in the intron regions.

Both the enhancer elements and promoter of a selectively expressed gene can be sequenced using standard DNA sequencing techniques, and can then be prepared as discrete units by oligonucleotide synthesis. An advantage of this approach is that suitable restriction sites for convenient ligation can be included. This approach also permits modifications to be made in the sequence which optimize the ability of these cis-acting elements to effect the desired level of expression. (It has already been seen that absolute coherence with the native sequence is not required for successful enhancement.) These sequences are amplified in cloning vectors using standard techniques, and ligated into expression vectors at desired locations using the general vector construction techniques described in ¶C below.

B.2. Location of the Enhancer Sequences

The differentiative enhancer sequences of the invention derived from the 5' flanking region in genes encoding endogenous cognate proteins are, in general, between positions about −1 and about −300. However, the exact position will depend on the particular gene examined. The location can be determined using methods described hereinbelow which illustrate selection of the appropriate enhancer portion of the 5' flanking sequence. Similar methods can be used to obtain enhancer sequences from any region of the gene.

Brifey, use is made of a "reporter", i.e., a protein which has an easily assayed activity and thus permits ready assessment of the level of its production in host cells. Transient assay can be used, as integration into the genome is not necessary or desirable for assessment of the results. Suitable viral or other compatible promoters are provided to obtain an expression system for the DNA sequence encoding the reporter protein. A particularly useful reporter protein is, for example, the gene encoding chloramphenicol acetyl transferase (CAT) an easily measureable enzyme activity (Gorman, et al. *Molec Cell Biol* (1982) 2:1044). (Alternatively, a protein to which labeled antibody has been prepared may be used to provide a measure of expression levels, although unless the protein is secreted, lysis is required for assay.)

The reporter sequences are operably linked to a suitable promoter, for example, a viral promoter such as the HSV TK promoter (McKnight, S. L., et al, *Science* (1982) 217:316) or the Rous Sarcoma Virus (RSV) promoter (see Gorman, C., et al. *Proc Natl Acad Sci* (USA) (1982) 79:6777, which describes pRBV CAT a vector having this linkage). Such vectors are preferably constructed so as to have a polylinker providing a plurality of restriction sites for the convenient insertion of the sequences to be assayed typically within about 1 kb upstream of the viral promoter.

To identify and diagnose the desired differentiative enhancer sequences, a portion of the selectively expressed gene is excised and assessed. For the 5' flanking regions an approximately 800 to 500 bp fragment extending from the region of about −800 to −500 to a position within the transcribed sequence, is removed from the gene for the selectively expressed cognate protein in the differentiated cell of origin. It is then ligated into the polylinker sequence upstream from a promoter, usually a viral promoter, in a vector containing an expression system for a reporter or sequence encoding another assayable protein. The vectors containing the insert are transformed into cells corresponding to the gene for the cognate protein, and, as controls, into cells which are compatible with the expression system, but which do not correspond to the cell-specialized gene. Successful transformants are screened using the reporter function within about 48 hr of transformation. Deletions are then made in the inserted fragment and the effect on the production of the reporter sequences in freshly transformed corresponding cells as compared to non-corresponding cells is assessed. Such assessment is made easier by employing the internal control of a comparative cotransfection technique as outlined in ¶B.3 below. However, in principle, comparisons can be made by employing larger numbers of experiments without the use of this internal control.

Since orientation is unimportant to the enhancing sequence's performance, inserts in either orientation are operable, and this property may be used to advantage in obtaining deletions both from the 5' and 3' ends of the insert, using analogous techniques. Plasmids representative of those with inserts in both orientations located about 1 kb upstream of the promoter are linearized with a restriction enzyme which cuts immediately downstream of the insert and the linear DNA is treated with exoIII and S1 to generate random deletions. Depending on the orientation of the insert, the deletion will be from the 5' or 3' end. The reaction mixture is then digested with a restriction enzyme which cuts proximally upstream of the viral promoter, the resulting fragment blunt ended, if necessary, using S1 nuclease, and the plasmid religated using blunt end conditions. After religation, the plasmids are again assessed as above by transforming cells of corresponding differentiation and comparing the expression level of the coding sequences for the reporter function with that obtained in non-corresponding cells, and with those obtained before the deletions were made. The location of the deletions is confirmed using standard techniques such as restriction analysis and sequencing. By obtaining a pattern of deletions which permits high levels of reporter function expression in corresponding as opposed to non-corresponding cells, the location of the enhancer sequence can be ascertained to within approximately 40 bp precision at both the 5' and 3' ends of the original insert.

In principle, it would be possible to locate the desired enhancer sequences by creating deletions in the isolated selectively expressed gene itself and retransforming the corresponding cells with vectors containing the genes bearing this series of deletions. However, the level of protein production assignable to the vector expression system would then need to be assessed against a background of endogenous expression. To utilize this method, some means would need to be available to distinguish the cognate protein produced by the vector from that natively produced by the cell. This could be done, in principle, by slightly altering the coding sequence for the protein contained in the vector permitting detection by immunoprecipitation of the resulting protein or, for example, by deleting the signal sequence from an ordinarily secreted protein permitting intracellular accumulation. This alternative approach, while possible, is less convenient and definitive than the foregoing use of reporter functions. The ease of assay for protein production is greatly diminished, and the DNA modification required to create distinguishability from the endogenous cognate protein may affect the results. Furthermore, enhancer sequences located within the promoter region could not be found in this manner, and effecting the desired deletions upstream of the promoter would be more complex.

B.3. An Improvement in the Method to Assess Enhancing Potential Using Reporter Function Activity It has been found that the procedure in ¶B.2 can be improved by providing an internal control vector to balance out the effect of transformation and expression efficiency on expression. In addition to the test vector, a suitable alternate expression vector containing a different reporter function is used to cotransfect the cells as an internal indicator to reflect differences in cell types with respect to DNA uptake and expression. For example, the DNA sequence encoding β-galactosidase under the control of RSV promoter has been successfully so used. It has been found that cotransformation yields a consistent pattern of expression for the unaltered cotransformed vectors regardless of cell type and that interference between the cotransforming vectors with respect to transformation or expression does not occur.

In this method, the test plasmid is cotransfected with the marker plasmid, and the level of expression for the test plasmid normalized against that of the marker. If the marker level of expression is decreased by, for example, 25% in a particular experiment, the base level of test plasmid expression (i.e., without enhancer sequences) is calculated to be depressed by 25% as well, and the enhancement factor over this base level is computed using this decreased expression as the measure of unenhanced expression. (Controls using cells which do not correspond to the origin of the test enhancer sequences give concommitant variations between marker and test vectors.)

B.4. Construction of Expression Vectors

A variety of approaches to vector construction can be used, depending on the components of the control module desired to be included. In all cases, the components may either be excised from their native selectively expressed gene, and, if desired, modified for insertion into expression vectors, or synthesized by oligonucleotide synthesis using, for example, automated procedures now commercially available.

If a differentiative promoter module is to be included, the coding sequence for a desired protein is operably linked to a promoter derived from a selectively expressed gene. The location of such promoter sequences is already known—i.e., from about −1 to about −110 in such genes. Sequences of a number of promoter regions is also already known—see, e.g., FIG. 3. The expression module can be further modified by the insertion of one or more enhancer sequences derived from the same selectively expressed gene as the promoter. The enhancer sequences will have been located as described in ¶B.2, and either prepared by excision or by alternate methods, such as by synthetic oligonucleotide preparation. The nucleotide sequences in the appropriate regions are also partially shown in FIG. 3, extended sequences for the ratI, ratII and human insulin gene 5' flanking regions are shown in FIG. 4, and for amylase and chymotrypsin in FIG. 5. The differentiative promoter/coding sequence if constructed in suitable cloning vectors, may then be excised and inserted into backbone vectors containing means for replication either by their being autonomously replicating as would be ordinarily the case for yeast vectors, or by containing sequences which permit the integration of the expression system, along with the enhancer module, into the genome of the host cell.

The enhancer sequences may be inserted adjacent the expression system either individually or as a pre-ligated unit into the target expression vector. The inserts may be in either orientation and either upstream or downstream of the expression system. The proximity of the enhancer module is not as critical as that of the promoter, as enhancers are still functional within approximately 2 kb. More proximal locations, and locations upstream of the expression system are preferred. It may be possible also to introduce some portions of the module to locations within the expression system. A particularly preferred construction contains the enhancers indigenous to the 5' flanking sequences in their native locations.

These vectors are then transformed into host cells which correspond to the specificity of the differentiative control module. Such cell lines are available in many cases from the American Type Culture Collection or, if necessary, can be prepared from suitable tissue by immortalizing primary cultures of such cells. Cells transformed with the specifically enhanced expression vectors are then grown under conditions suitable for the hosts and the protein produced recovered, if desired, by standard means appropriate to the protein produced. The procedures of culture growth and protein isolation are readily available and well understood, and do not form part of the invention. Modification of culture conditions to obtain optimal growth may be desirable in some cases.

The enhancer module portion may contain differentiative enhancer sequences, preferably derived from the 5' flanking region, but may also include downstream sequences in the selectively expressed gene. Combinations of these and multiple copies of one or more of these sequences may also be used in the expression vector. The module of the invention thus can be constructed in a variety of strengths so that the expression can be regulated at a multiplicity of levels.

C. Standard Methods

C.1. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by 1 unit of enzyme in about 20 μl of buffer solution; in the samples herein, typically, an excess of restriction enzyme is used to ensure complete digestion of the DNA substrate. Incubation times of about 1 hr to 2 hr at about 37° C. are workable, although variations can be tolerated. After each incubation, protein is removed by extraction with phenol/chloroform, optionally followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the 4 deoxynucleotide triphophates (dNTPs) using incubation times of about 15 to 25 min at 20° to 25° C. in 50 mM Tris pH 7.6, 50 mM NaCl, 6 mM MgCl$_2$, 6 mM DTT and 5–10 μM dNTPs. The Klenow fragment fills in at 5' sticky ends but chews back protruding 3' single strands, even though the 4 dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Exonuclease III attacks double-stranded DNA, but hydrolyzes beginning at the 3' end of the nucleotide sequence. Thus, digestion of a double-stranded DNA results in two 5' protruding ends. Hydrolysis is carried out in a buffer containing 15 mM Tris, pH 8, 10 mM NaCl, 1 mM MgCl$_2$, and 0.1 mM DTT, using approximately 2000 units per μl exonuclease III. Ordinarily, 150 units of exonuclease III were used to react with 10 μg DNA.

Synthetic oligonucleotides are prepared by the triester method of Matteucci, et al, *J Am Chem Soc* (1981) 103:3185–3191) or by commercially available oligonucleotide synthesis. Kinasing of single strands prior to annealing or for labeling is achieved using an excess, e.g., approximately 10 units of polynucleotide kinase to 1 nmole substrate in the presence of 50 mM Tris, pH 7.6, 10 mM MgCl$_2$, 5 mM dithiothreitol, 1–2 mM ATP, 1.7 pmoles $^{32}$P ATP (2.9 mCi/mmole), 0.1 mM spermidine, 0.1 mM EDTA.

Ligations are performed in 15–30 μl volumes under standard conditions and temperatures: 20 mM Tris-Cl pH 7.5, 10 mM MgCl$_2$, 10 mM DTT, 33 μg/ml BSA, 10 mM–50 mM NaCl, and either 40 μM ATP, 0.01–0.01 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 mM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per μg of vector at 60° for about 1 hr. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

C.2. Verification of Construction

In the constructions set forth below, correct ligations for plasmid construction are confirmed by transforming *E. coli* strain HB101, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (USA) (1969) 62:1159, following chloramphenicol amplification (Clewell, D. B., *J Bacteriol* (1982) 110:667). The isolated DNA is analyzed by restriction and/or sequenced by the dideoxy method of Sanger, F., et al, *Proc Natl Acad Sci* (USA) (1977) 74:5463 as further described by Messing, et al, *Nucleic Acids Res* (1981) 9:309, or by the method of Maxam, et al, *Methods in Enzymology* (1980) 65:499.

C.3. Hosts

Host strains used in cloning and expression herein are as follows: Cloning and analysis of plasmid construction by restriction and/or sequencing utilized the bacterial host *E. coli* HB101. Eucaryotic cells used as hosts to assess expression levels are: HIT cells, which correspond to the cell-specialized insulin gene; AR4-2J cells, which correspond to the chymotrypsin, amylase, or trypsin gene, and CHO and BHK cells, which do not correspond to either of the cell-specialized genes used as sources for the enhancing sequences illustrated below. These hosts are further described in ¶D.1.

Of course, other bacterial hosts can be used for cloning and verification of construction; a number of conveniently available *E. coli* strains are deposited with ATCC. Similarly, other selectively expressed genes such as those for hemoglobin, crystallin or immunoglobulin, would require suitable corresponding hosts derived from respectively, red blood cells, lens cells, or lymphocytes, or cell lines derived therefrom.

C.4. Transformations

Depending on the host cell used, transformation is done using standard techniques, appropriate to such cells. For mammalian cells without cell wall barriers, the calcium phosphate precipitation method of Graham and van der Eb, *Virology* (1978) 52:546 is preferred. Transformations into yeast can be carried out according to the method of Van Solingen, P., et al, *J Bact* (1977) 130:946 or Hsiao, C. L., et al, *Proc Natl Acad Sci* (USA) (1979) 76:3829.

D. Examples

The following examples are intended to illustrate the invention but not to limit it.

D.1. Nature of 5' Flanking Sequences of Selectively Expressed Genes

D.1.a. Confirmation of 5' Flanking Differentiative Control Sequences

Applicants' recent publication has demonstrated the presence of 5' flanking sequences which behave as differentiative control sequences for both insulin and chymotrypsin genes of human and rat origin. See Walker. M. D., et al, *Nature* (1983) 306:5943, incorporated herein by reference. Briefly, the presence of differentiative properties was shown by linking the 5' flanking sequences from the insulin and chymotrypsin genes to the coding sequence of chloramphenicol acetyl transferase (CAT). Expression vectors were constructed by operably linking the CAT coding sequence to 5' flanking sequences of various lengths from rat insulin I, human insulin, rat chymotrypsin B, and to rat growth hormone (as negative control) and comparing expression to that obtained from vectors where the CAT sequence was placed under the control of the TK or RSV promoter (as positive controls).

Each of the plasmids constructed was tested in each of 3 host cell types: CHO cells, a fibroblast line derived from Chinese hamster ovary (which represents a control host corresponding to the neither the chymotrypsin nor insulin sequences), HIT cells, a transformed line from hamster pancreatic endocrine cells that produces insulin at 2–5% of the rate of endocrine β-cells (which represents a differentiated cell corresponding to the insulin sequence) and AR4-2J cells, a rat exocrine pancreas tumor line that contains about 10% of the level of chymotrypsin mRNA of the adult rat pancreas (which represents a cell corresponding to the chymotrypsin sequence).

The results obtained showed that while vectors using the TK promoter produced CAT at levels consistently lower than those expressed under RSV promoter control, the amounts produced were a constant percentage of the control regardless of host. The vectors containing the 5' flanking regions of the rat insulin and human insulin gene on the other hand produced CAT in significant amounts only in HIT cells; the sequences associated with rat chymotrypsin only in AR4-2J, cells and the 5' flanking sequences for rat growth hormone were comparatively inactive in all three cell types. Accordingly, the 5' flanking regions of both insulin and chymotrypsin contain cell specific sequences which are operable only in corresponding cell types.

In more detail, the vector used for insertion of sequences to be analyzed for cell-specific control activity was designated pBR CAT. This vector was constructed by isolating a 1.6 kb HindIII/BamHI fragment which included the entire CAT coding sequence splice sites and polyadenylation signals which was excised from pSVO CAT (Gorman, C. J., et al, *Molec Cell Biol* (1982) 2:1044). This fragment was ligated into the vector fragment from HindIII/BamHI digested pBR322, thus placing a ClaI cleavage site immediately upstream from the HindIII site of the inserted fragment. The following inserts were made at the HindIII site:

A PvuII/RsaI fragment of the rat insulin 1 gene comprising 410 bp of a flanking DNA, 43 bp of exon 1, and 6 bp of intron 1;

An NcoI/NcoI fragment of the human insulin gene comprising 879 bp of flanking DNA, 42 bp of exon 1, 179 bp of intron 1 and 20 bp of exon 2;

An EcoRI/HindIII fragment from rat chymotrypsin gene comprising 709 bp upstream flanking DNA (from −711 to −3):

An EcoRI/XhoI fragment from rat growth hormone gene (as a control) comprising 1.6 kb of flanking DNA and 8 bp of exon 1:

A BamHI/BglII fragment of the TK gene comprising 109 bp of flanking DNA and 41 bp of the single TK exon.

For the plasmid containing the CAT sequence under control of the RSV promoter, the construct used was pRSV CAT which contains 524 bp of the RSV 3' long terminal repeat ligated at the HindIII site of pSVO CAT.

The foregoing vectors were transformed into the aforementioned three types of cell lines, using the calcium phosphate precipitation method of Graham and van der Eb (supra). Four hr after addition of the transforming DNA, the cells were subjected to 20% glycerol for 2 min and then collected 44 hr after addition of the DNA. Extracts were prepared by sonication and centrifugation, and CAT assays were performed essentially according to the method of Gorman, C. M., et al, *Molec Cell Biol* (supra). The reactions were allowed to proceed for up to 60 min (CHO and HIT cells) or 12.5 hr (AR4-2J). In the longer reactions, a higher initial concentration of acetyl coenzyme A (4.4 mM) was necessary to preserve linearity. Samples were extracted with 1 ml ethyl acetate, the solution was dried down and the residue dissolved in 20 μl ethyl acetate and analyzed by ascending TLC using chloroform/methanol (95:5 v/v), and assayed by radioautography. Results expressed as percent conversions of $^{14}C$ chloramphenicol to $^{14}C$ chloramphenicol acetate were normalized to the levels of expression obtained using the RSV promoter as shown in Table 1a below:

TABLE 1a

| Fragment | Cell Type | | |
|---|---|---|---|
| | CHO | HIT | AR4-2J |
| RSV | 100 | 100 | 100 |

TABLE 1a-continued

| Fragment | Cell Type | | |
|---|---|---|---|
| | CHO | HIT | AR4-2J |
| TK | 15 | 14 | 17 |
| Rat insulin | 1.2 | 71 | <0.4 |
| Human insulin | <0.1 | 4 | ND |
| Rat chymotrypsin | 0.9 | 0.2 | 42 |
| Rat growth hormone | <0.1 | <0.2 | ND |

These results show that the 5' flanking sequences of the selectively expressed genes were effective only in cells corresponding to those of their origin.

D.1.b Localization of the 5' Flanking Differentiative Control Sequences

Deletions in the 5' portion of the inserts were made in the plasmids whose construction is described in ¶D.1.a in order to localize the effective differentiative control sequences in rat insulin, human insulin, and rat chymotrypsin. Where appropriate restriction sites were present within the insert, that site was cleaved by the appropriate restriction enzyme and ligated to the unique ClaI site located immediately upstream of the HindIII site in the pBR CAT plasmid. Sites thus employed were the XmnI site at −370 and −247 in the rat insulin gene, the PstI site at −159 in the rat insulin gene, the PstI site at −334 in the human insulin gene, the PvuII site at −258 and the BglII site at −168 in the human insulin gene, and the SacI sites at −274 and −93 and the NcoI site at −192 in the rat chymotrypsin gene.

Other deletions were produced by exoIII digestion to give truncations at −302 and −219 in the rat insulin gene. These exoIII digestions were carried out by first inserting a 548 bp fragment of plasmid DNA, with a unique BglII site located 5 bp from one of its ends, into the ClaI site of pBR CAT. The intermediate plasmid was linearized with BglII, and treated successively with exoIII, S1 nuclease, ClaI, DNA polymerase 1 (Klenow) and T4 DNA ligase to obtain these deleted plasmids. The deleted plasmids were then assessed for expression activities in the corresponding cell types as set forth in ¶D.1.a, and the activity recorded in Table 1b below as referenced against the activity of the undeleted sequence set at 100. The results show that the rat insulin differentiative control sequences are located downstream of −302; those of human insulin downstream of −258; and those of rat chymotrypsin downstream of −274.

TABLE 1b

| | Deletion | Activity (%) |
|---|---|---|
| Rat insulin | −410 | 100 |
| | −370 | 92 |
| | −302 | 122 |
| | −247 | 11 |
| | −219 | 1 |
| | −159 | 0.5 |
| Human insulin | −879 | 100 |
| | −334 | 83 |
| | −258 | 110 |
| | −168 | 11 |
| Rat chymotrypsin | −711 | 100 |
| | −274 | 97 |
| | −192 | 9 |
| | −93 | 7 |

D.2. Differentiative Enhancers

D.2.a. Demonstration of Enhancer Activity in the 5' Flanking Sequences of a Selectively Expressed Gene A comparison of the rat insulin I −410 to +51 sequence ability to enhance expression with that of the murine sarcoma virus (MBV) and Rous sarcoma virus (RSV) enhancer was shown by constructions wherein these sequences are placed upstream of the TK promoter for CAT expression. The results of expression in corresponding (HIT) and non-corresponding (BHK and CHO) cells are shown (BHK cells are baby hamster kidney fibroblasts, obtainable from ATCC) in Table 2:

TABLE 2

| Enhancer | Promoter | Cell Line | | |
|---|---|---|---|---|
| | | HIT | BHK | CHO |
| — | TK | 1 | 1 | 1 |
| rIns | TK | 40 | 1.0 | 1.1 |
| MSV | TK | 7.6 | 7.4 | 1.9 |
| RSV | TK | 6.5 | 11.3 | 3.6 |

Thus while MSV and RSV sequences are effective in enhancing expression mediated by the TK promoter in all host cells, albeit to varying extents, the rIns sequences are effective only in their corresponding cell type.

D.2.b. Localization of the Diffentiative Enhancer Sequences

In order conveniently to locate enhancer elements for rat insulin 1, as described below, or for other genes, pLSTK1 was constructed as shown in FIG. 2. pLSTK1 contains the CAT coding sequence under the control of the herpes TK promoter, and also contains a polylinker containing HindIII and XbaI sites about 600 bp upstream from the TK promoter fragment.

To prepare the starting plasmids, pLSTK1 was cleaved with HindIII and ligated to the −420 to +51 bp PvuII/RsaI rat insulin I fragment of the rat insulin gene (Cordell, B., et al, Cell (1979) 18:533) using HindIII linkers to obtain pLSTK1-X and pLSTK1-Y. Each derivative vector was shown by suitable restriction techniques to contain the fragment insert—one of the two possible orientations was present in X, and the other in Y, pLSTK1-X and pLSTK1-Y were used to transform HIT cells and gave expression levels for CAT three fold higher than those shown by cells transformed by pLSTK1. An internal control using an RSV-beta-Gal expression system was used to obtain normalization for transfection efficiency. This was done by cotransfecting cells with the appropriate CAT construct and with a plasmid containing β-galactosidase coding sequences under the control of the RSV promoter (5 µg each). The activity of β-galactosidase was measured at pH 8, and the CAT activity normalized against the β-galactosidase activity.

The fragment inserts were moved closer to the TK promoter by treating the plasmids with XbaI and with NruI (the NruI site is located at the 5' end of the TK promoter fragment) and religation. The resulting plasmids showed expression of CAT eight times that of pLBTK1. It was also shown that the inserted insulin fragment produced a five fold increase in CAT activity when placed about 1.7 kb downstream of the TK cap site.

Thus, it is apparent that while the ability of the sequences to enhance expression under the TK promoter is relatively insensitive to position, there are preferred locations with respect to the expression system. These preferences are at present empirical.

pLSTK1-X and pLBTK1-Y were treated with XbaI to linearize the DNA, and then with exoIII and S1 to generate sets of deletions in the insulin sequence. Of course, since both orientations were represented, both 5' and 3' deletions were obtained. The mixture was then digested with NruI, and blunt-end ligated to fuse the remainders of the insulin sequences to the 5' end of the TK promoter. The resulting ligation mixture was used to transform *E. coli* HB101 and the plasmids isolated and analyzed by restriction analysis and sequencing.

The resulting plasmids having various deletions at the 5' and 3' ends of the inserted fragment were than used to transform HIT calls. The results are shown in Table 3.

TABLE 3

| Deletion | | % Activity |
| --- | --- | --- |
| | None | 100 |
| 5' | −333 | 147 |
| | −287 | 81 |
| | −249 | 79 |
| | −219 | 22 |
| | −114 | 4 |
| 3' | −103 | 170 |
| | −150 | 37 |
| | −198 | 38 |
| | −249 | 3 |
| no sequences from rat insulin | | 2.5 |

These data suggest that the majority of enhancing activity is located between nucleotides −103 to −249. When such fragment is tested (see D.3) it, indeed, is found to show at least 70% of the activity of the parental −420 to +51 fragment.

In a strictly analogous manner, the 5' flanking sequence of rat chymotrypsin B (Bell, G. I., et al, unpublished results) were excised, provided with HindIII linkers, and inserted into the HindIII site of the linker in pLSTK1. Deletions were made as set forth above for the rat insulin gene, and the resulting activity assessed in AR4-2J cells with the results shown in Table 4.

TABLE 4

| Chymotrypsin B | |
| --- | --- |
| Region | Activity* |
| −275/−93 | 100% |
| −225/−113 | 60 |
| −225/−137 | 42 |
| −225/−150 | 19 |
| −225/−170 | 15 |
| no chymotrypsin sequence: | 2 |

*Relative to −275/−93 Fragment = 100%

These results show that at least these sequences between −225 and −137 are required for appreciable activity.

Similarly, in experiments performed using the RsaI fragment −234 to −41 of the amylase gene inserted into pLSTK1 at the HindIII site, the data in Table 5 were obtained.

TABLE 5

| Amylase | |
| --- | --- |
| 5' Deletion | Activity |
| −234 | 100 |
| −199 | 102 |
| −175 | 115 |
| −171 | 76 |
| −166 | 82 |
| −154 | 117 |
| −140 | 5 |
| no amylase sequences | 2 |

TABLE 5-continued

| Amylase | |
| --- | --- |
| 3' Deletion | Activity |
| −41 | 100 |
| −77 | 25 |
| −92 | 21 |
| −100 | 27 |
| −115 | 23 |
| −159 | 3 |
| −179 | 4 |
| no amylase sequences | 2 |

These data indicate that the 5' boundary of activity is approximately −154, and the 3' boundary at approximately −115.

Using analogous techniques, the 5' flanking region of the trypsin gene has been similarly mapped.

D.3. Preparation of a Vector Containing the Differentiative Expression Module

The differentiative enhancer sequences of the 5' flanking portion of the rat insulin 1 gene are prepared as a 147 bp −249 to −103 fragment excisable from its host vector as a SacI fragment by preparing the source vector in a three-way ligation using the following three components:

1) pLSTK1 partially digested with SacI and BAPped;
2) a SacI/PstI digest of pLSTK1-3'∇103 (i.e. the original plasmid deleted at the 3' end to −103) followed by isolation of the 56 bp fragment spanning positions −159 to −103; and
3) a PstI/SacI digest of pLSTK1-5'∇249 followed by isolation of the approximately 90 bp fragment containing nucleotides −249 to −159.

The ligation mixture is transformed into *E. coli* HB101, and plasmid DNA isolated. This can serve as a source of the SacI fragment, and also of the combination of the enhancer module with a downstream TK promoter.

The excised SacI fragment is ligated into a vector containing an expression system for leukocyte interferon under the control of the TK promoter by insertion into a polylinker preceding the TK promoter which controls the expression of the IFN coding sequences. The resulting enhanced expression vector is then transformed into HIT cells. The resulting transformed cells show increased amounts of leukocyte interferon production as compared with those transformed with the unenhanced expression vector.

Alternatively, a 147 bp enhancer containing DNA fragment having the nucleotide sequence for positions −249 to −103 of the rat insulin I gene, as shown in FIG. 4, is prepared by chemical synthesis using commercial automated oligonucleotide synthesis techniques to obtain overlapping portions of complementary single strands, followed by treatment of the annealed strands with DNA polymerase. Suitable restriction sites are included in the oligomer synthesis for ligation into expression vectors.

D.4. Verification and Location of a Differentiative Promoter Sequence pLSTK1-A is a vector containing the CAT sequences in operable linkage to the rat insulin 1 promoter, but with the sequences from the rat insulin 5' flanking portion upstream from the PstI site at −114 bp are removed. It is incapable of promoting detectable transcription initiation for the CAT sequences in transformed HIT cells, presumably because the upstream enhancer elements are not present. This vector was modified by inserting an MSV (viral) enhancer-containing fragment upstream from the rat insulin 1 fragment. This insertion resulted in the expression of CAT in HIT cells at levels comparable to those obtained with MSV enhancer linked to the TK promoter used as a control. However, the combination of MSV enhancer with the rat insulin (−114 to +51) region was not able to effect expression of CAT in BHK cells, a non-corresponding cell line. The −114 to +51 region was not capable of appreciably enhancing the activity of the TK promoter in either HIT or BHK cell lines. These data are shown in Table 6. pLSTK1 was used as an unenhanced control.

TABLE 6

| Vector | Enhancer | Promoter | Relative Activity HIT | BHK |
|---|---|---|---|---|
| pLSTK1 | — | TK | 1 | 1 |
|  | MSV | TK | 7.6 | 7.4 |
| pLSTK1-A | — | rIns (−114 to +51) | <0.1 | <0.1 |
|  | MSV | rIns (−114 to +51) | 40 | 0.1 |
|  | rIns (+51 to −114) | TK | 1.8 | 1.2 |

These data show that the proximal 5' flanking sequences contribute to cell-specific expression by virtue of activity that is position dependent and/or integral to the rat insulin 1 promoter.

D.5. Summary

Differentiative enhancer regions may be found in the 5' flanking sequences of cell-specialized genes or in positions downstream therefrom. While the enhancer abilities of these segments is relatively independent of orientation and position with respect to a targeted expression system comprising at least a promoter operably linked to coding sequences, preferential orientations and positions relative to the system may be empirically determined. In addition, the expression system may have, as its promoter, a differentiative promoter module also derived from a cell-specialized selectively expressed gene. The invention thus provides differentiative control modules for expression which comprise differentiative promoter, differentiative enhancer, or both. These may be ligated into operable linkage with codons for a desired protein in expression vectors to obtain superior expression of the coding sequence in host cells corresponding to the origin of the differentiative control module.

We claim:

1. A mammalian tissue-specific DNA fragment comprising a heterologous DNA molecule encoding a gene of interest; and a tissue-specific transcription-enhancing DNA segment isolated from an insulin gene, wherein said segment is contained within a 5' flanking region located −1 to about −300 bases upstream of the transcription initiation site of the insulin gene, said transcription-enhancing DNA segment being positioned within about 2 kb of the heterologous DNA molecule and operatively linked upstream to a DNA promoter segment, said promoter segment being positioned upstream of and operatively linked to the heterologous DNA molecule, whereby when the tissue-specific DNA fragment is placed in an insulin-producing cell, expression of the heterologous protein is enhanced relative to the level of expression in a differentiated cell of a different tissue type.

2. A recombinant vector comprising a eukaryotic vector capable of being expressed in a mammalian cell and the tissue-specific, expression enhancing DNA segment of claim 1.

3. An insulin-producing mammalian host cell comprising the vector of claim 2.

4. An improved method of enhancing expression of a heterologous protein by culturing the host cell of claim 3 in an expression medium allowing the enhanced expression of the protein to occur, and recovering said protein.

5. A mammalian tissue-specific DNA fragment comprising a heterologous DNA molecule encoding a gene of interest; and a tissue-specific transcription-enhancing DNA segment isolated from a chymotrypsin gene, wherein said segment is contained within a 5' flanking region located −1 to about −300 bases upstream of the transcription initiation site of the chymotrypsin gene, said transcription-enhancing DNA segment being positioned within about 2 kb of the heterologous DNA molecule and operatively linked upstream to a DNA promoter segment, said promoter segment being positioned upstream of and operatively linked to the heterologous DNA molecule, whereby when the tissue-specific DNA fragment is placed in an chymotrypsin-producing cell, expression of the heterologous protein is enhanced relative to the level of expression in a differentiated cell of a different tissue type.

6. A recombinant vector comprising a eukaryotic vector capable of being expressed in a mammalian cell and the tissue-specific, expression enhancing DNA segment of claim 5.

7. A chymotrypsin-producing mammalian host cell comprising the vector of claim 6.

8. An improved method of enhancing expression of a heterologous protein by culturing the host cell of claim 7 in an expression medium allowing the enhanced expression of the protein to occur, and recovering said protein.

9. A mammalian tissue-specific DNA fragment comprising a heterologous DNA molecule encoding a gene of interest; and a tissue-specific transcription-enhancing DNA segment isolated from an amylase gene, wherein said segment is contained within a 5' flanking region located −1 to about −300 bases upstream of the transcription initiation site of the amylase gene, said transcription-enhancing DNA segment being positioned within about 2 kb of the heterologous DNA molecule and operatively linked upstream to a DNA promoter segment, said promoter segment being positioned upstream of and operatively linked to the heterologous DNA molecule, whereby when the tissue-specific DNA fragment is placed in an amylase-producing cell, expression of the heterologous protein is enhanced relative to the level of expression in a differentiated cell of a different tissue type.

10. A recombinant vector comprising a eukaryotic vector capable of being expressed in a mammalian cell and the tissue-specific, expression enhancing DNA segment of claim 9.

11. An amylase-producing mammalian host cell comprising the vector of claim 10.

12. An improved method of enhancing expression of a heterologous protein by culturing the host cell of claim 11 in an expression medium allowing the enhanced expression of the protein to occur, and recovering said protein.

* * * * *

UNITED STATES PATENT AND TRADEMARK OFFICE
CERTIFICATE OF CORRECTION

PATENT NO. : 5,486,462
DATED : January 23, 1996
INVENTOR(S) : William J. Rutter, et al It is certified that error appears in the above-identified patent and that said Letters Patent is hereby corrected as shown below:

Column 4, line 1, delete "pLSTK1." and insert --pLSTK1. The left region is NruI to EcoRI of pBR 322 (-3.4kb) (NruI converted to BamHI). The CAT region at the lower right is CAT coding DNA + SV40 splice + polyadenylation signals (HIII to BamHI from pSVO CAT - see Gorman Mol. Cell Biol. The Tkp is a SacI fragment containing a fully active TK promoter (-109 to +50). The BamHI region is NruI from pBR 322 (600bp). The polylinker at the upper right is a polylinker (-60bp) containing the following in clockwise order: EcoRI, ClaI, HindIII, XbaI, BglII, PstI, SalI, BamHI, (ClaI, HindIII, XbaI, BglII are unique sites).--.

Column 13, line 56, delete "to the neither" and insert --to neither--.

Column 16, line 1, delete "(MBV)" and insert --(MSV)--.

Column 16, line 24, delete "conveniently to" and insert --to conveniently--.

Signed and Sealed this

Ninth Day of September, 1997

Attest:

BRUCE LEHMAN

Attesting Officer

Commissioner of Patents and Trademarks